(12) United States Patent
Munro et al.

(10) Patent No.: US 6,592,898 B2
(45) Date of Patent: Jul. 15, 2003

(54) BIOADHESIVE COMPOSITIONS COMPRISING HYDROPHOBIC POLYMERS

(75) Inventors: Hugh Semple Munro, Chipping Camden (GB); Mohammed Yasin, Saltley (GB)

(73) Assignee: First Water Limited, Marlborough (GB)

( * ) Notice: Subject to any disclaimer, the term of this patent is extended or adjusted under 35 U.S.C. 154(b) by 0 days.

(21) Appl. No.: 09/771,004

(22) Filed: Jan. 26, 2001

(65) Prior Publication Data
US 2002/0034492 A1 Mar. 21, 2002

Related U.S. Application Data

(63) Continuation of application No. PCT/GB99/02516, filed on Jul. 30, 1999.

(30) Foreign Application Priority Data

Jul. 31, 1998 (GB) ............................................... 9816826
Mar. 24, 1999 (GB) ............................................... 9906700
Apr. 23, 1999 (GB) ............................................... 9909348

(51) Int. Cl.⁷ ............................ A61K 9/14; A61K 31/74
(52) U.S. Cl. ....................... 424/484; 424/486; 424/488; 424/77; 424/78.08
(58) Field of Search ................................ 424/484, 486, 424/488, 77, 78.08

(56) References Cited

U.S. PATENT DOCUMENTS

| 4,527,087 A | 7/1985 | Taya et al. | |
| 4,539,996 A | 9/1985 | Engel | |
| 4,554,924 A | 11/1985 | Engel | |
| 4,848,353 A | 7/1989 | Engel | |
| 5,012,810 A | 5/1991 | Strand et al. | |
| 5,173,302 A | 12/1992 | Holmblad et al. | 424/448 |
| 5,338,490 A * | 8/1994 | Dietz et al. | 252/500 |
| 5,665,391 A * | 9/1997 | Lea | 424/484 |
| 5,670,557 A | 9/1997 | Dietz et al. | 522/184 |

FOREIGN PATENT DOCUMENTS

| EP | 0012402 A1 | 6/1980 | ........................ 3/14 |
| EP | 0085327 | 8/1983 | ............ A61B/5/04 |
| EP | 0676457 A1 | 10/1985 | .................... 133/14 |
| EP | 0188381 | 7/1986 | ............ H01B/1/12 |
| WO | WO93/01746 | 2/1993 | ............ A61B/4/02 |
| WO | WO09/24149 | 7/1997 | ............ A61L/15/58 |
| WO | WO97/34947 | 9/1997 | ............. C08K/5/00 |

OTHER PUBLICATIONS

PCT International Search Report for Application No. PCT/GB99/02516 dated Dec. 7, 1999.
Search Report for Briitish Patent Application No. GB9816826.3 dated Feb. 9, 1999.

* cited by examiner

Primary Examiner—Thurman K. Page
Assistant Examiner—Blessing M. Fubara
(74) Attorney, Agent, or Firm—Palmer & Dodge LLP; Kathleen M. Williams

(57) ABSTRACT

Bioadhesive compositions which comprise a hydrophobic polymer wherein the concentration of the polymer at the surface of the adhesive is greater than its concentration in the bulk of the adhesive are described; and biomedical electrodes, fixation products and wound dressings containing them.

69 Claims, 5 Drawing Sheets

BIOADHESIVE COMPOSITIONS COMPRISING HYDROPHOBIC POLYMERS

This is a continuation of PCT/GB99/02516 filed on Jul. 30, 1999

This invention relates to bioadhesive compositions, particularly electrically conductive hydrogel compositions having bioadhesive properties. The invention further relates to biomedical skin electrodes incorporating such hydrogel bioadhesive compositions that are electrically conductive.

BACKGROUND

Biomedical skin electrodes are widely used in a variety of situations, whenever for example it is required to establish an electrical connection between the surface of the body of the patient and external medical equipment for transmission of electrical signals.

Modern medicine uses many medical procedures where electrical signals or currents are received from or delivered to a patient's body. The interface between medical equipment used in these procedures and the skin of the patient is usually some sort of biomedical electrode. Such electrodes typically include a conductor which must be connected electrically to the equipment, and a conductive medium adhered to or otherwise contacting skin of the patient, and they are of varying types with a wide variety of design configurations which will generally depend on their intended use and whether for example they are to be used as transmission electrodes or sensing i.e. monitoring electrodes.

Among, the therapeutic procedures using biomedical electrodes are transcutaneous electric nerve stimulation (TENS) devices used for pain management; neuromuscular stimulation (NMS) used for treating conditions such as scoliosis; defibrillation electrodes to dispense electrical energy to a chest cavity of a mammalian patient to defibrillate heart beats of the patient; and dispersive electrodes to receive electrical energy dispensed into an incision made during electrosurgery.

Among diagnostic procedures using biomedical electrodes are monitors of electrical output from body functions, such as electrocardiograms (ECG) for monitoring heart activity and for diagnosing heart abnormalities.

For each diagnostic, therapeutic, or electrosurgical procedure, at least one biomedical electrode having an ionically conductive medium containing an electrolyte is adhered to or is otherwise contacted with mammalian skin at a location of interest and is also electrically connected to electrical diagnostic, therapeutic, or electrosurgical equipment. A critical component of the biomedical electrode is the conductive medium which serves as the interface between the mammalian skin and the diagnostic, therapeutic, or electrosurgical equipment, and which is usually an ionically conductive medium.

Biomedical electrodes are used among other purposes to monitor and diagnose a patient's cardiovascular activity. Diagnostic electrodes are used to monitor the patient immediately and, are only applied to the patient for about five to ten minutes. Monitoring electrodes, however, are used on patients in intensive care for up to three days continuously. In contrast, Holter electrodes are used to monitor a patient during strenuous and daily activities.

Although all of the biomedical electrodes just referred to are used to record cardiovascular activity, each electrode requires specific features or characteristics to be successful. Thus, the diagnostic electrode does not have to remain adhered to a patient for extensive periods but it does have to adhere to hairy, oily, dry and wet skin effectively for the five to ten minutes of use. The monitoring electrode has to adhere for a longer period of time although the patient is often immobile during the monitoring period. The Holter electrodes is susceptible to disruption from adhesion due to physical motion, perspiration, water, etc., and therefore requires the best adhesion and at the same time comfort and electrical performance.

In the biomedical electrodes known in the prior art the ionically conductive medium which serves as an interface, between the skin of a mammalian patient and the electrical instrumentation, ranges from conductive gels and creams to conductive pressure sensitive adhesives. However, while the conductive media can be in the form of pressure sensitive conductive adhesives, for monitoring or Holter biomedical electrode use such conductive adhesives are not generally adequate on their own to maintain adhesion to mammalian skin and additional hypoallergenic and hydrophobic pressure sensitive adhesives may be employed around the conductive medium to provide the required mammalian skin adhesion. U.S. Pat. No. 5,012,810 (Strand et al.) and U.S. Pat. Nos. 4,527,087, 4,539,996, 4,554,924 and 4,848,353 (all Engel) are examples of documents that disclose biomedical electrodes which have a hydrophobic pressure sensitive adhesive surrounding the conductive medium.

The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490. The method of preparation described therein involved casting a mixture (as a solution and or suspension) consisting of the hydrophilic polymer containing phase and hydrophobic components onto a substrate and then removing the solvent.

In general, a desirable skin electrode is one which maintains good electrical contact with the skin and is free of localised current hot spots, i.e. exhibits uniform conductivity. For example, it has been found that a prior art electrode utilising karaya gum tends to creep in use and flatten out, exposing skin to possible direct contact with the current distribution member or lead wire. A desirable skin electrode should also usually have a low electrical impedance.

It is an object of this invention to provide hydrogel skin adhesives possessing enhanced adhesive properties which may be readily varied to suit different uses and, in the case of medical electrodes or similar devices; different configurations or applications. It is also an object of the invention to provide such hydrogel skin adhesives which in addition may possess superior electrical characteristics as compared to those commonly associated with bioadhesive hydrogels.

SUMMARY OF THE INVENTION

According to the invention there is provided a bioadhesive composition which comprises an aqueous plasticised three dimensional polymeric matrix and a hydrophobic polymer wherein the concentration of the polymer at the surface of the matrix is greater than its concentration in the bulk of the matrix. The matrix is preferably in the form of a hydrogel.

The performance of hydrogels as adhesives is related to the surface energetics of the adhesive and of the adherend (for example mammalian skin) and to the viscoelastic response of the bulk adhesive. The requirement that the adhesive wets the adherend to maximise the work of adhesion is well known. This requirement is generally met when the adhesive has a similar or lower surface energy to the adherend. The viscoelastic properties, in particular the elastic or storage modulus (G') and the viscosity modulus (G") are important. They are measured by dynamic mechanical testing at different rad/s. Their values at low rad/s (approximately 0.01 to 1 rad/s) and high rad/s (100 to 1000 rad/s) has been related to the wetting/creep behaviour and peel/quick stick properties respectively. The choice, assembly and processing of the ingredients of the hydrogel adhesive are usually targeted at making a material with a balance of properties suitable for pressure sensitive adhesive applications. A balance between the quantities and nature of polymer, plasticiser and the degree of crosslinking/entanglement has to be achieved.

The main electrical property of interest is the impedance. Performance standards have been drawn up by the American Association of Medical Instruments (AAMI). In sensing electrode applications the electrodes, consisting of the hydrogel adhesive and a suitable conductive support, are placed in pairs, adhesive to adhesive contact. The conductive support frequently has a Ag/AgCl coating in contact with the adhesive. The measured impedance is dependent on both the quality of the Ag/AgCl coating and the adhesive. In this configuration the adhesive must contain chloride ions. The concentration of chloride ions influences the impedance such that increasing the concentration can lower impedance. It would be anticipated that the activity of the ions (as opposed to the concentration) would be important in determining impedance, but in practice the determination of ion activity in these systems is not a trivial matter. It has been found that as an important requirement in the control of impedance is the water content and its related activity, and in general adhesives with higher water activity have lower impedances.

When water is lost from the hydrogel both the adhesive and electrical properties are likely to change deleteriously. Whilst the presence of glycerol or other polyhydric alcohols in other reported formulations has been quoted to provide humectant properties to the hydrogel, it has been found that the most important parameter to preventing water loss is the activity of the water within the hydrogel which in turn depends on the nature and proportions of the other components and manner of processing.

Water activity in the hydrogel adhesive is primarily dependent on the water content and the nature of the polymeric components and the way in which they are processed. Water activity has been shown to have a better correlation with the growth of bacteria and moulds than water content. It has been found that organisms struggle to grow at water activities less than 0.8. Enzyme activity has also been reported to decrease significantly below activity of 0.8. Water activity has also been found to influence the adhesivity of the hydrogel adhesive in that at water activities above about 0.75, they become less adhesive. A bioadhesive composition having a suitable balance of the characteristics discussed above has now surprisingly been found.

Accordingly the bioadhesive composition is preferably characterised in that it has:
  (i) a water activity of from 0.4 to 0.9;
  (ii) an elastic modulus at 1 rad/s of from 700 to 15,000 Pa;
  (iii) an elastic modulus at 100 rad/s of from 2000 to 40,000 Pa;
  (iv) a viscous modulus at 1 rad/s of from 400 to 14,000 Pa;
  (v) a viscous modulus at 100 rad/s of from 1000 to 35,000 Pa;
wherein the viscous modulus is less than the elastic modulus in the frequency range of from 1 to 100 rad/s. Preferably the impedance at 500 MHz is less than 10 ohms, more preferably less than 5 ohm. When the composition includes chloride ions, the impedance at 10 Hz on Ag/AgCl electrodes is less than 1000 ohm, preferably less than 500 ohm.

Examination of the rheological properties of the compositions have been successfully used to characterise and differentiate adhesive behaviour. Typically the elastic modulus (G') and the viscous modulus (G") are measured over a range of 0.01–100 rad/s at a given temperature. For skin applications the appropriate temperature is 37° C. The moduli at low rad/s values relate to the initial bonding of the adhesive to skin and the higher to the changes in moduli values associated with de-bonding. Methods of measuring G' and G" are well known; for example a Rheometric Scientific RS-5 rheometer could be used.

The water activity of the composition can be measured using impedance methods with devices such as the Rotronic AWVC (manufactured by Rotronic). The activity of water may also be determined by placing the composition in environments of controlled humidity and temperature and measuring the changes in weight. The relative humidity (RH) at which the composition does not change weight corresponds to the activity of water in the gel (RH/100). The use of saturated salt solutions to provide the appropriate environmental conditions is well known. All compositions directly exposed to relative humidities less than that corresponding to the activity of water will be thermodynamically allowed to lose water. Exposure to greater relative humidities and the composition will gain weight.

The impedance values at 10 Hz can be measured as follows. Silver/Silver chloride electrodes are assembled from the compositions by placing 25 mm by 25 mm samples onto silver/silver chloride coated plastic eyelets (product of Micron Medical Products and marketed as plastic eyelets 107). The impedances of the compositions are recorded by contacting the electrodes face to face via the compositions and connecting to an Xtratek ET-65A ECG electrode tester (product of Xtratek of Lenexa, Kans.). The impedance at 500 MHz can be measured using an impedance meter from a 10 cm by 5 cm section of gel 0.5 cm thick placed between two conducting aluminium plates.

The bioadhesive composition according to the invention preferably comprises an aqueous plasticiser, a polymer of one or more monomers comprising a hydrophilic unsaturated water soluble acrylamido monomer, and a hydrophobic polymer.

The bioadhesive composition according to the invention is preferably obtainable by polymerising an aqueous reaction mixture comprising
  (a) one or more monomers comprising a hydrophilic unsaturated water soluble acrylamido monomer; and
  (b) a hydrophobic polymer.

The bioadhesive composition is preferably obtainable by polymerising a reaction mixture comprising from 20% to 55% by weight of (a), from 0.1% to 10% by weight of (b), the remainder of reaction mixture comprising water.

The bioadhesive composition according to the invention preferably is such that the relative amount of hydrophobic polymer (which is the amount of hydrophobic polymer relative to the amount of monomer) is preferably at least four times greater, more preferably at least eight times greater, at the surface of the composition compared to what it is in the bulk of the composition. The relative amount at the surface is preferably the relative amount in the composition at a depth of up to 1 micron (as measured using FTIR ATR using a ZnSe crystal), preferably up to 0.25 micron (as measured using FTIR ATR using a Germanium crystal). The relative amount is measured by obtaining the ratio of the peak height of the peak in the carbonyl region for the hydrophobic polymer to the peak height of the peak in the carbonyl region for the monomer, using the relevant FTIR ATR technique. The wave number values for the relevant peaks for the hydrophobic polymer and the monomer are well known.

More preferably, the ratio of the relative amount in the surface of the composition at a depth of up 0.25 micron to the relative amount in the surface of the composition at a depth of up 1 micron is more than 1:1, more preferably more than 1.25:1, most preferably more than 1.5:1.

According to the invention there is further provided a biomedical electrode which comprises a bioadhesive composition according to the invention in association with an electrically conductive interface. The biomedical electrode optionally further comprises a support. The electrically conductive interface preferably comprises a layer of electrically conductive material which is preferably applied to the support, when present.

The invention also provides a fixation product suitable for attaching a biomedical device to skin (or the human body) e.g. a catheter, tubing, wires or cables which product comprises a bioadhesive composition according to the invention.

According to the invention, there is further provided a wound dressing which comprises a carrier material and the bioadhesive composition according to the invention. The carrier material is either encapsulated or coated by either of the bioadhesive compositions. Preferably it is coated, particularly on only one side.

According to the invention there is also provided a process for the preparation of a wound dressing according to the invention which process comprises either:

(a) coating or encapsulating a carrier material with an aqueous reaction mixture comprising the said first monomer, the said second monomer and a crosslinking agent, and curing the coating on the material; or (b) coating a carrier material with the bioadhesive composition according to the invention.

In preferred embodiments the first and second monomers will be acrylate based monomers selected for their ability to polymerise rapidly in water and having substantially the same molecular weight whereby in a mixture of the two the relative proportions may be varied without significantly altering the molar characteristics of the composition.

The monomer is preferably a compound of formula

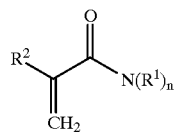

(I)

wherein n represents 2 or 3 (where n represents 3, a counter anion is also present which is preferably a halide ion, especially chloride), $R^1$ represents H, $C_{1-4}$-alkyl or $R^8SO_3M$, $R^8$ represents an optionally substituted hydrocarbon moiety, $R^2$ is hydrogen or optionally substituted methyl and ethyl, and M represents hydrogen or a cation. When n represents 2, $R^1$ preferably represents a hydrogen atom and $R^8SO_3M$.

When n represents 3, $R^1$ preferably represents a hydrogen atom and/or $C_{1-4}$-alkyl, more preferably $R^1$ represents methyl.

$R^8$ is preferably an optionally substituted alkyl, cycloalkyl) or aromatic moiety. Preferably $R^8$ represents a saturated moiety or an aromatic moiety. $R^8$ preferably contains from 3 to 12 carbon atoms, more preferably from 3 to 6 carbon atoms. A preferred moiety which $R^8$ represents is

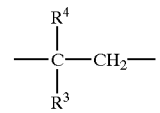

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

A suitable additional monomer is preferably a compound of formula

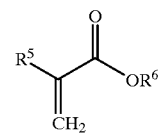

(II)

wherein $R^5$ represents hydrogen or optionally substituted methyl or ethyl, $R^6$ represents hydrogen, a cation or $R^7SO_3$ wherein $R^7$ represents an optionally substituted alkylene moiety of 1 to 4 carbon atoms. Preferably $R^7$ represents optionally substituted n-propyl.

$R^1$, $R^2$, $R^3$, $R^4$, $R^5$, $R^7$ and $R^8$ are optionally substituted by a group which preferably has a tendency to increase the water solubility of the compound. Suitable groups will be well known to a person of skill in the art. A preferred optional substituent is a hydroxyl, amino or ammonium group or a halogen (e.g. chlorine, bromine, or iodine) atom. A suitable cation is an alkali metal cation, especially sodium or potassium.

Preferably, the acrylamido monomer is 2-acrylamido-2-methylpropanesulphonic acid or an analogue thereof or one of its salts, e.g. an alkali metal salt such as a sodium, potassium or lithium salt or (3-acrylamidopropyl) trimethyl ammonium chloride (sold as a 78% aqueous solution by Aldrich). The particularly preferred acrylamido monomer is the sodium salt of 2-acrylamido-2-methylpropanesulphonic acid, commonly known as NaAMPS.

Preferably the one or more monomers (a) additionally comprise an ionic hydrophilic unsaturated water-soluble monomer which is more preferably an acryl monomer and/or an acryl sulphonate monomer. It is more preferably acrylic acid or an ester or salt thereof and/or a polymerisable sulphonate or a salt, e.g. an alkali metal salt such as a sodium, potassium or lithium salt, of acrylic acid (3-sulphopropyl)ester or an analogue thereof. The particularly preferred monomer is acrylic acid (3-sulphopropyl) ester potassium salt, commonly known as SPA.

NaAMPS is available commercially at present from Lubrizol as either a 50% aqueous solution (reference code LZ2405) or a 58% aqueous solution (reference code LZ2405A). SPA is available commercially in the form of a solid from Raschig.

The total monomer content in the aqueous reactive mixture is preferably from 15% to 60% by weight, preferably from 20% to 50% by weight.

The plasticiser used in the invention is an aqueous plasticiser which optionally additionally includes a polyhydric alcohol (e.g. glycerol) and/or a polymeric alcohol (e.g. polyethylene oxide).

The hydrophobic polymer is preferably a hydrophobic pressure sensitive adhesive. A suitable hydrophobic pressure sensitive adhesive is a polyacrylate, polyolefin, silicone adhesive, natural or synthetically derived rubber base or a polyvinyl ether or a blend thereof. Preferably the hydrophobic pressure sensitive adhesive is an a vinyl acetate dioctyl maleate copolymer and/or an ethylene/vinyl acetate copolymer. Ethylene/vinyl acetate copolymer such as that designated DM137 available from Harlow Chemicals or vinyl acetate dioctyl maleate such as that designated Flexbond 150 and sold by Air Products is particularly preferred. Those skilled in the art will also know that the molecular weight and comonomer ratios may be altered to control the properties of hydrophobic pressure sensitive adhesives.

The advantage of incorporating a hydrophobic polymer in the compositions according to the invention is that the hydrophobic component segregates to the surface (as determined by Fourier transform infrared attenuated total reflectance spectroscopy, FTIR ATR, approximate sampling depth 0.5 microns). It has been found that Fourier transform infrared attenuated total reflectance spectroscopy spectra (FTIR ATR) of the pregel mixture before polymerisation and of the gel formed after polymerisation using a ZnSe crystal (approximate sampling depth 1 $\mu$m) show markedly different relative amounts of the monomer and the hydrophobic polymer. It is the amount of the hydrophobic component present in the surface that influences the adhesion to a wide variety of materials. The greater the amount of the hydrophobic component in the surface the greater the adhesion. In hydrogel adhesives of between 100 to 2000 microns thick made in accordance with the present invention, ratios of hydrophilic to hydrophobic components ranging from 7:1 to 1:30 preferably from 6:1 to 1:20 have been found to be preferable, especially when these ratios are present in the surface of the adhesive composition. In the process of the present invention, however, it may take up to 72 hours from the initial curing of the adhesive hydrogel for the segregation of the hydrophobic materials to the surface, as defined by the ATR sampling depth, to be complete. In general, the degree of surface segregation exhibited by such hydrophobic pressure sensitive adhesive (HPSA) will be dependent on factors such as the composition of the HPSA, viscosity of the pre-gel mixture, temperature and rate of curing.

Conventional crosslinking agents are preferably used to enhance the mechanical stability and to control the adhesive properties of the composition. Typical crosslinkers include tripropylene glycol diacrylate, ethylene glycol dimethacrylate, alkoxylated triacrylate, polyethylene glycol diacrylate (PEG400 or PEG600), methylene bis acrylamide.

The aqueous reactive mixture optionally further comprises a surfactant, an electrolyte, a processing aid (which is preferably a hydrophobic polymer), a water soluble polymer suitable for forming an interpenetrating polymer network, an antimicrobial agent (e.g. citric acid, stannous chloride) and/or, for drug delivery applications, pharmaceutically active agents, the latter being designed to be delivered either passively (e.g. transdermally) or actively (e.g. iontophoretically) through the skin.

The process used to prepare bioadhesive compositions in accordance with the invention comprises mixing the ingredients to provide a reaction mixture in the form of an initial pre-gel aqueous based liquid formulation, which is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer an siliconised release paper or other solid substrate. The processing will generally be carried out in a controlled manner involving a precise predetermined sequence of mixing and thermal treatment or history. One preferred feature of the process according to the invention is that no water is removed from the hydrogel after manufacture.

Plasticiser

The compositions according to the invention generally comprise, in addition to a crosslinked polymeric network, an aqueous plasticising medium and, optionally, additional electrolyte. Plasticisers are generally used in the invention to control adhesive properties.

The aqueous plasticising medium optionally additionally comprises a polymeric or non-polymeric polyhydric alcohol (such as glycerol), an ester derived therefrom and/or a polymeric alcohol (such as polyethylene oxide). Glycerol is the preferred plasticiser. An alternative preferred plasticiser is an ester derived from boric acid and a polyhydric alcohol (such as glycerol). The aqueous reactive mixture preferably comprises from 10% to 50%, preferably from 10% to 45%, of plasticiser (other than water) by weight of the mixture.

It is well known that water in hydrogels can be present in at least two forms, freezing and non-freezing, as measured by Differential Scanning Calorimetry. In many examples of commercially available hydrogels the water is present only as non freezing water. It has been found, however, that compositions with useful adhesive properties comprising the first and second monomers can be made which have both freezing and non-freezing water, and the water activity in such gels is generally high. One advantage of including the second monomer is that it has a tendency to increase the likelihood that the compositions will contain freezing water. The advantage gained by the presence of freezing water becomes evident in the application of these gels to stress monitoring ECG. In certain cases the preferred medium for interfacing the monitoring instrument with the body is a "wet gel". It has been suggested that the advantage gained by "wet gels" is in the wetting of the skin and consequent lowering of skin impedance, but it has been found in clinical trials that hydrogels with freezing water can match the performance of "wet gels".

Electrolyte

When the compositions are intended for use in conjunction with A/AgCl medical electrodes, chloride ions are required to be present in order for the electrode to function. Accordingly the compositions preferably include an electrolyte except where the composition comprises an additional monomer which is a cationic monomer in the form of a chloride salt. Potassium chloride and sodium chloride are commonly used. However, any compound capable of donating chloride ions to the system may be used, for example lithium chloride, calcium chloride, ammonium chloride. The amount that should be added is dependent on the electrical properties required and is typically from 0.2 to 7% by weight. In designing the compositions for lowest impedance as measured under the AAMI standard, allowance must be given for the amount and activity of water. These factors will control the effective ion activity and hence the amount of chloride available for participating in the electrochemistry of the system. Compositions with lower chloride concentration but higher water activity have lower impedances.

Interpenetrants

The compositions preferably additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesised and/or crosslinked in the presence of the other. As will be appreciated, this combination will generally be a physical combination rather than a chemical combination of the two polymers. IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

It has been found that polymerisings and crosslinking water soluble monomers in the presence of water soluble polymers, water and polyhydric alcohols produces hydrogel materials with enhanced rheological and consequently adhesive properties.

Suitable water soluble polymers for the formation of semi IPN's include poly (2-acrylamido-2-methylpropanesulphonic acid) or one of its salts and its copolymers, poly (acrylic acid-(3-sulphopropyl) ester potassium salt), copolymers of NaAMPS and SPA, polyacrylic acid, polymethacrylic acid, polyethylene oxide, polyvinyl methyl ether, polyvinyl alcohol, polyvinyl-pyrrolidone, its copolymers with vinyl acetate, dimethylaminoethyl methacrylate, terpolymers with dimethylaminoethyl methacrylate and vinyl-caprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

The amount of interpenetrant polymer used will be dependent on the mechanical and rheological properties required as well on consideration of processing conditions. If the interpenetrant polymer used increases the viscosity of the pre-gel mix beyond 5000 centipoise it has been found that the monomers do not polymerise and crosslink on an acceptable time scale (should be less than 60 seconds, preferably less than 10 seconds). The viscosity depends on the nature and molecular weight of the interpenetrant and the nature of pre-gel processing.

Of the natural polysaccharides, gum arabic or maltodextrin is usually preferred due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can be critical with respect to the properties of the manufactured hydrogel. For a given formulation, if the components are assembled at 25° C. and cured different electrical and adhesive properties are obtained compared to those that have been heated to 70° C. Whilst adhesive properties may be enhanced, electrical properties e.g. low frequency impedance, can be downgraded. Solutions containing natural polysaccharides become less opaque indicative of improved solubility. The activity of water in compositions prepared from heat treated pre-gels generally is lower than in non heat treated pre-gels.

Surfactant

The composition according to the invention optionally includes a surfactant.

Any compatible surfactant may be used. Nonionic, anionic and cationic surfactants are preferred, either alone or in combination. The surfactant is preferably included in an amount from 0.1% to 20% by weight, more preferably 0.1% to 10% by weight.

Carrier Material

The carrier material used in the wound dressings according to the invention is preferably perforated. Generally any conventional carrier material known for use in dressings can be used as the carrier material. It is preferable that the carrier material is made from inelastic fibres, preferably continuous inelastic fibres. The carrier material is generally either knitted, extruded, woven or non-woven. It is optionally in the form of for example, a foam or a film. The smallest dimension of each perforation in the carrier material is preferably from 0.5 to 5.0 mm, more preferably from 1.0 to 3.0 mm. The fibres are made from cotton, rayon, polyester, polyamide, polypropylene, polyamide or wool or a mixture thereof.

Preparation of Wound Dressing

There are a variety of possible ways in which the process of the invention may be carried out.

Examples of ways in which process (a) may be performed include extruding the aqueous reaction mixture onto a web which, in the case of an automated process, is preferably moving. The web is preferably made from paper, polyester, polyolefin or any other material commonly used in the art. The carrier material is either laid on top of the aqueous reaction mixture after it has been extruded or is laid on top of the web and the aqueous reaction mixture is extruded over it. The assembly is then cured. Where the carrier material is perforated, it may be necessary to blow air through the assembly before curing to ensure that the perforations are free from the bioadhesive composition.

An alternative way in which process (a) according to the invention may be carried out is by coating the carrier material with the aqueous reaction mixture by, for example, dipping the carrier material in a bath of the aqueous reaction mixture and then passing the coated carrier material over or round a single roller or through a nip roller. The assembly is then cured. Again, if the carrier material is perforated, it may be necessary to blow air through the assembly before curing to ensure that the perforations are free from the bioadhesive composition.

Process (b) according to the invention may be performed, for example, by laminating a sheet of the bioadhesive composition with the carrier material. The sheet of bioadhesive composition is preferably supported by a plastic or coated material to act as a protective release sheet.

In both processes according to the invention, the aqueous reaction mixture is preferably coated in an amount of from 0.1 to 2 kg/m$^{2}$.

The wound dressing according to the invention is optionally coated on one or both sides with at least one release sheet. The release sheets are generally either made of plastic or coated paper e.g. siliconised paper.

The bioadhesive compositions according to the invention are also useful in a variety of consumer care applications. For example they can be used as the adhesive for a faecal management device or prosthesis, e.g. hair prosthesis.

The invention will be further described with reference to the following Examples in connection with bioadhesive compositions suitable for use in medical skin electrodes, in wound dressings or in fixation products.

EXAMPLE 1

Figure 1:
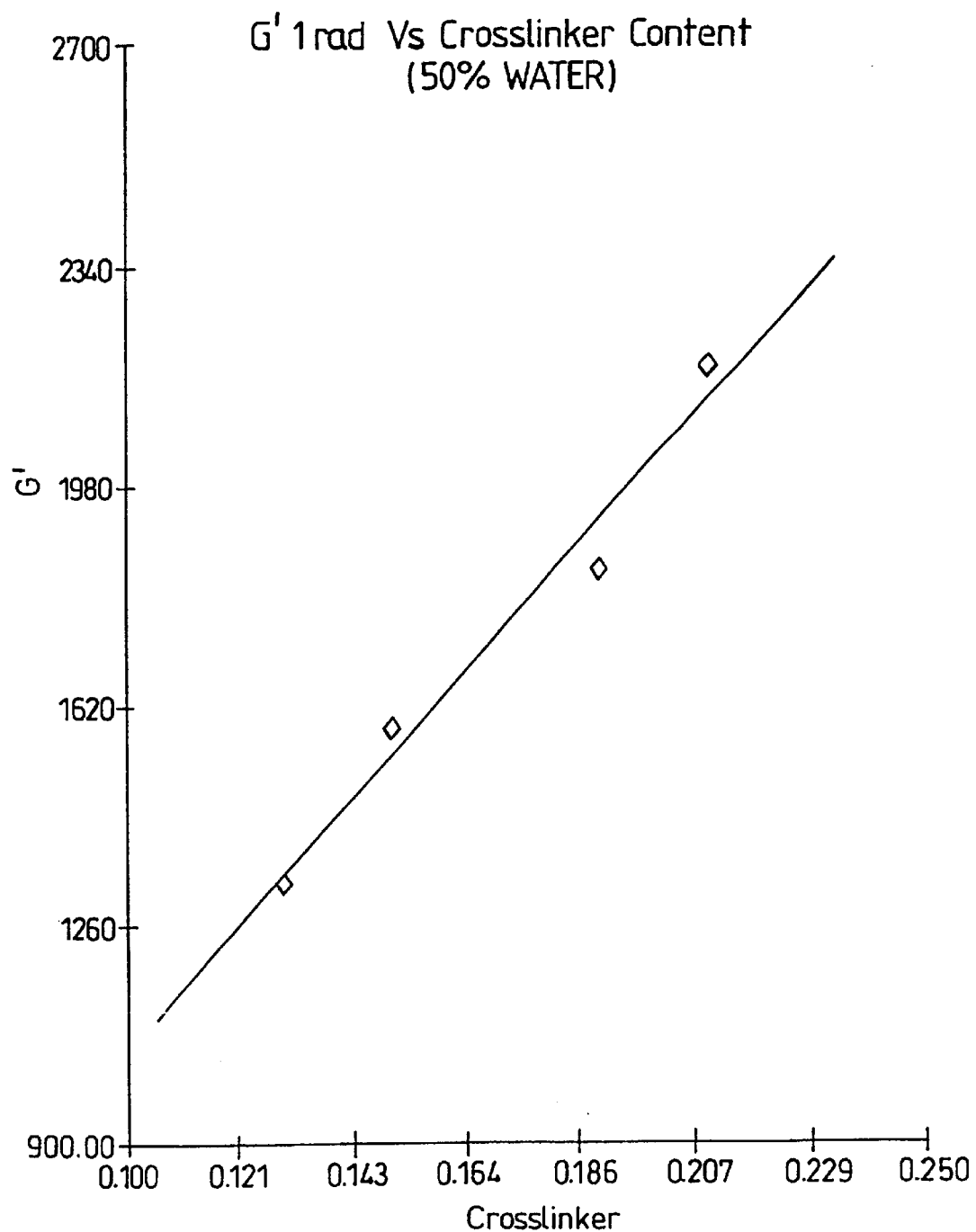
FIG. 1 is a graph showing the change in elastic modules G with respect to the amount of cross-linking agent used according to one embodiment of the invention.

To 20 parts glycerol, 3 parts of a hydrophobic ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture were added 50 parts of a 58% solution of the sodium salt of 2-acrylamido-2-methylpropane sulphonic acid (NMPS) (LZ2405A), 16 parts potassium salt of 3-sulphopropyl acrylate (SPA) and 5 parts potassium chloride, and the solution was heated with stirring to 60° C. for one hour. The mixture had changed from an opaque off white to a translucent off white appearance. The turbidity of the solutions as measured in a portable turbidity meter, product code H193703 marketed by Hanna had changed from 254 ftu to 107 ftu. The solution was cooled to 20° C. and then there was added 0.13 parts of a solution A which solution contains 20 parts of polyethylene glycol diacrylate (pEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) had been dissolved. This final solution was stirred for one hour and then was coated onto siliconised release paper at a coat weight of 0.8 kilograms per square meter and exposed to ultraviolet radiation by being passed under a medium pressure mercury arc lamp at a speed of 5 meters per minute to form clear self supporting gels. The residence time under the lamp was 4 seconds. The storage moduli (G') of 20 mm diameter discs stamped from the gels were recorded on a Rheometric Scientific RS-5 rheometer at 37° C. Silver/Silver chloride electrodes were assembled from the gels by placing 25 mm by 25 nm samples onto silver/silver chloride coated plastic eyelets (product of Micron Medical Products and marketed as plastic eyelets 107). The impedances of the gels were recorded by contacting the gelled electrodes face to face via the gels and connecting to an Xtratek ET-65A ECG electrode tester (product of Xtratek of Lenexa, Kans.). The resulting gel had an impedance of 254 Ohms and a G' value at 1 rad of 5328. The activity of water in the gel, as determined by placing the gel into cabinets at varying levels of humidity at 40° C. (40, 52, 64 and 80% RH) and measuring weight uptake or loss and extrapolating to zero weight change, was 0.62. Analysis of the gel by attenuated total reflectance infra-red spectroscopy revealed that in the surface regions (ca 0.5 microns), either the air surface or the surface in contact with the release paper, the concentration of the ethylene/vinyl acetate copolymer relative to the NaAMPS was significantly enhanced compared to the bulk composition.

EXAMPLE 2

To 20 parts glycerol, 3 parts of gum arabic, 3 parts of an ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture 50 parts of a 58% solution of the sodium salt of 2-acrylamido-2-methylpropane sulphonic acid (NaAMPS) (LZ2405A), 16 parts potassium salt of 3-sulphopropyl acrylate (SPA) and 5 parts potassium chloride were added and heated with stirring to 70° C. for one hour. The mixture changed from an opaque off white to a translucent off white appearance. The solution was cooled to 25° C. and then there were added 0.13 parts of solution A prepared as described in Example 1. This final solution was then stirred for one hour and then cured as in Example 1. The resulting gel had an impedance of 358 Ohms and a G' value at 1 rad of 5406. The activity of water as determined by the method in Example 6 was 0.55. The adhesion to skin of this gel was significantly greater than those described in the previous examples. Analysis of the gel by attenuated total reflectance infra-red spectroscopy revealed that in the surface region (ca. 0.5 microns), either the air surface or the surface in contact with the release paper, the concentration of the ethylene/vinyl acetate copolymer relative to the NaAMPS was significantly enhanced compared to the bulk composition.

EXAMPLE 3

To 30 parts glycerol, 5 parts of gum arabic, 10 parts of an ethylene/vinyl acetate copolymer emulsion (50% solids) (product of Harlow Chemicals marketed under the trade name DMI37) were added and stirred until a uniform colour was obtained. To this mixture 55 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.15 parts of a solution B which solution contains 20 parts of polyethylene glycol diacrylate (pEG600) (product of UCB Chemicals marketed under the trade name designation of Ebacryl 11) in which 2 parts of 1-hydroxycyclohexyl phenyl ketone (product of Ciba and marketed under the trade name designation of Irgacure 184) were dissolved. This final solution was then stirred for one hour and then cured as in Example 1.

EXAMPLE 4

To 45 parts glycerol, 5 parts of gum arabic, 0.2 parts of karaya gum, 5 parts of an ethylene/vinyl acetate copolymer emulsion (50% solids) (product of Harlow Chemicals marketed under the trade name DM137) were added and stirred until a uniform colour was obtained. To this mixture 45 parts of a 58% solution of the sodium salt of 2-acrylamido-2-methylpropane sulphonic acid (NaAMPS) (LZ2405A) and 2 parts potassium chloride were added and heated with stirring to 70° C. for one hour. The mixture changed from an opaque off white to a translucent off white appearance. The solution was cooled to 25° C. and then there were added 0.2 parts of solution B prepared as described in Example 3. This final solution was then stirred for one hour and then cured as in Example 1.

EXAMPLE 5

To 30 parts glycerol, 5 parts of gum arabic, 10 parts of an ethylene/vinyl acetate copolymer emulsion (50% solids)

(product of Harlow Chemicals marketed under the trade name DM137) were added and stirred until a uniform colour was obtained. To this mixture 55 parts of a 50% solution of the sodium salt of 2-acrylamido-2-methylpropane sulphonic acid (N S) (LZ2405) and 3 parts potassium chloride were added and heated with stirring to 70° C. for one hour. The mixture changed from an opaque off white to a translucent off white appearance. The solution was cooled to 25° C. and then there were added 0.15 parts of solution B prepared as described in Example 3. This final solution was then stirred for one hour and then cured as in Example 1

EXAMPLE 6

To 30 parts glycerol, 5 parts of gum arabic, 0.2 parts of karaya gum, 10 parts of an ethylene/vinyl acetate copolymer emulsion (50% solids) (product of Harlow Chemicals marketed under the trade name DM137). To this mixture 55 parts of a 58% solution of the sodium salt of 2-acrylamido-2-methylpropane sulphonic acid (NaAMPS) (LZ2405A), 0.2 parts potassium salt of 3-sulphopropyl acrylate (SPA) and 5 parts potassium chloride were added and heated with stirring to 70° C. for one hour. The mixture changed from an opaque off white to a translucent off white appearance. The solution was cooled to 25° C. and then there were added 0.15 parts of solution A prepared as described in Example 1. This final solution was then stirred for one hour and then cured as in Example 1.

EXAMPLE 7

To 30 parts glycerol, 5 parts of gum arabic, 0.2 parts of karaya gum, 10 parts of an ethylene/vinyl acetate copolymer emulsion (50% solids) (product of Harlow Chemicals marketed under the trade name DM137) were added and stirred until a uniform colour was obtained. To this mixture 55 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.15 parts of solution B prepared as described in Example 3. This final solution was then stirred for one hour and then cured as in Example 1.

EXAMPLE 8

To 20 parts glycerol, 5 parts of gum arabic, 0.2 parts of karaya gum, 10 parts of an ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture 55 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.15 parts of solution B prepared as described in Example 3. This final solution was then stirred for one hour and then cured as in Example 1.

EXAMPLE 9

To 30 parts glycerol, 0.2 parts of karaya gum, 5 parts of gum arabic and 10 parts of an ethylene/vinyl acetate copolymer emulsion (50% solids) (product of Harlow Chemicals marketed under the trade name DMI37) were added and stirred until a uniform colour was obtained. To this mixture 55 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.14 parts of solution B prepared as described in Example 3. This final solution was then stirred for one hour and then cured as in Example 1.

EXAMPLE 10

To 30 parts glycerol, 5 parts of gum arabic and 10 parts of an ethylene/vinyl acetate copolymer emulsion (50% solids) (product of Harlow Chemicals marketed under the trade name DM137) were added and stirred until a uniform colour was obtained. To this mixture 55 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.145 parts of solution B prepared as described in Example 3. This final solution was then stirred for one hour and then cured as in Example 1.

EXAMPLE 11

To 36 parts glycerol, 3 parts of gum arabic and 5 parts of an ethylene/vinyl acetate copolymer emulsion (50% solids) (product of Harlow Chemicals marketed under the trade name DM137) were added and stirred until a uniform colour was obtained. To this mixture 56 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.15 parts of solution A prepared as described in Example 1. This final solution was then stirred for one hour and then cured as in Example 1.

EXAMPLE 12

To 21 parts glycerol, 3 parts of gum arabic, 5 parts of an ethylene/vinyl acetate copolymer emulsion (50% solids) (product of Harlow Chemicals marketed under the trade name DM137) and 15 parts polyethylene glycol (molecular weight 600) were added and stirred until a uniform colour was obtained. To this mixture 56 parts of a 58% solution of the sodium salt of 2-acrylamido-2-methylpropane sulphonic acid (NaAMPS) (LZ2405A) were added and heated with stirring to 70° C. for one hour. The mixture changed from an opaque off white to a translucent off white appearance. The solution was cooled to 25° C. and then there were added 0.15 parts of solution A prepared as described in Example 1. This final solution was then stirred for one hour and then cured as in Example 1.

EXAMPLE 13

The formulations shown in Tables 1 and 2 were prepared using the following method which is for formulation 13a. To 20 parts glycerol, 15 parts of a hydrophobic vinyl acetate/dioctyl maleate copolymer emulsion (product of Air Products marketed under the trade name Flexbond 150) were added and stirred until a uniform colour was obtained. To this mixture were added 44 parts of a 58% solution of the sodium salt of 2-acrylamido-2-methylpropane sulphonic acid (NaAMPS) (LZ2405A), 20 parts potassium salt of 3-sulphopropyl acrylate (SPA) and 4 parts potassium chloride, and the solution was heated with stirring to 60° C. for one hour. The solution was cooled to 20° C. and then there was added 0.13 parts of solution C which solution which contains 20 parts of polyethylene glycol diacrylate (molecular weight 400) (product of UCB Chemicals marketed under the trade name designation of IRR 280) in which 6 parts of 1-hydroxycyclohexyl phenyl ketone (product of Ciba and marketed under the trade name designation of Irgacure 184) are dissolved. This final solution was stirred for one hour and then cured as in Example 1. The G' and G" moduli were measured from 20 mm diameter discs of the gel using a Rheometric Scientific RS-5 rheometer at 37° C.

Figure 2:
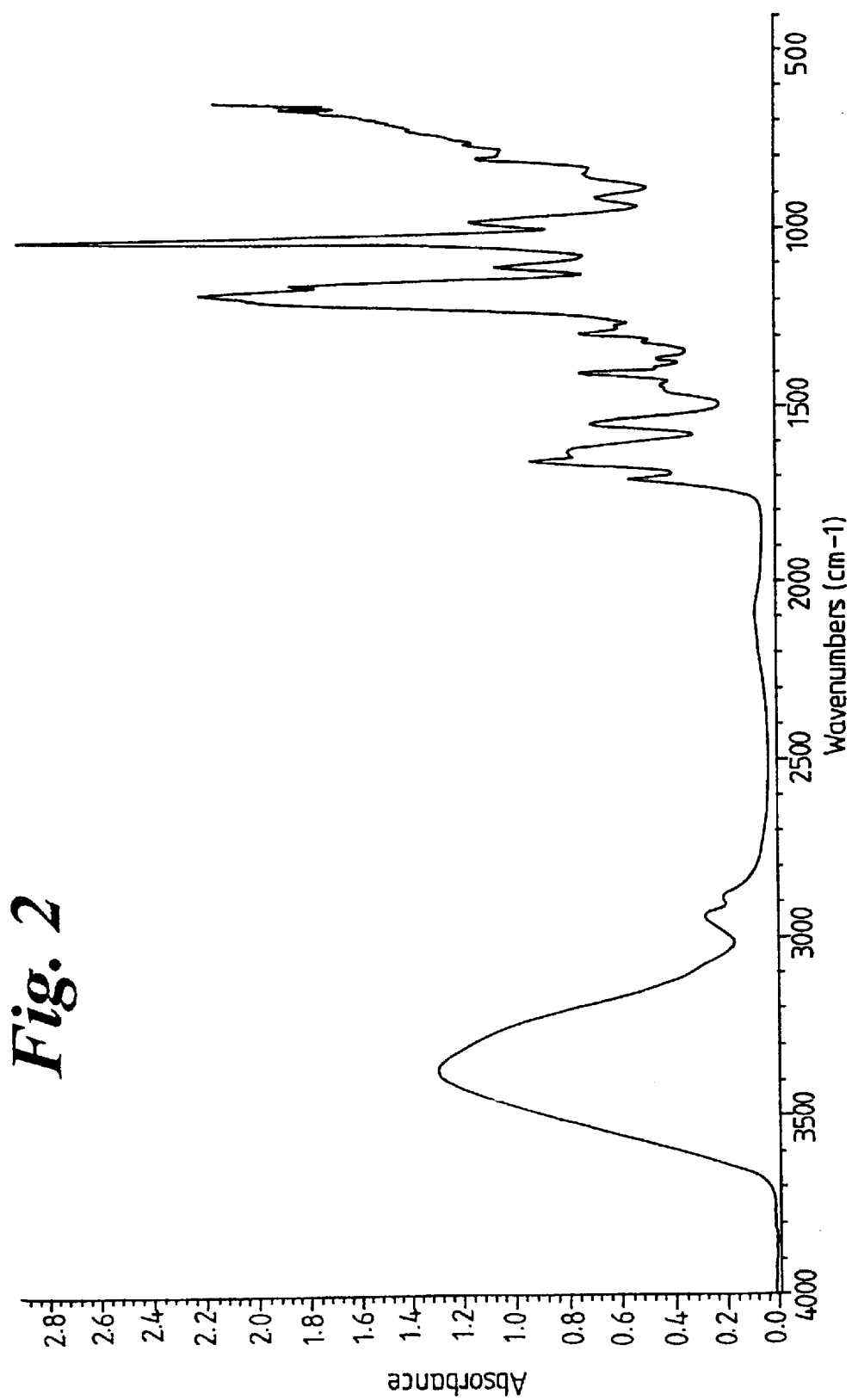
FIG. 2 is a graph showing Fourier transform infrared attenuated total reflectance spectra (FTIR ATR) of the pregel mixture according to one embodiment of the invention.
Figure 3:
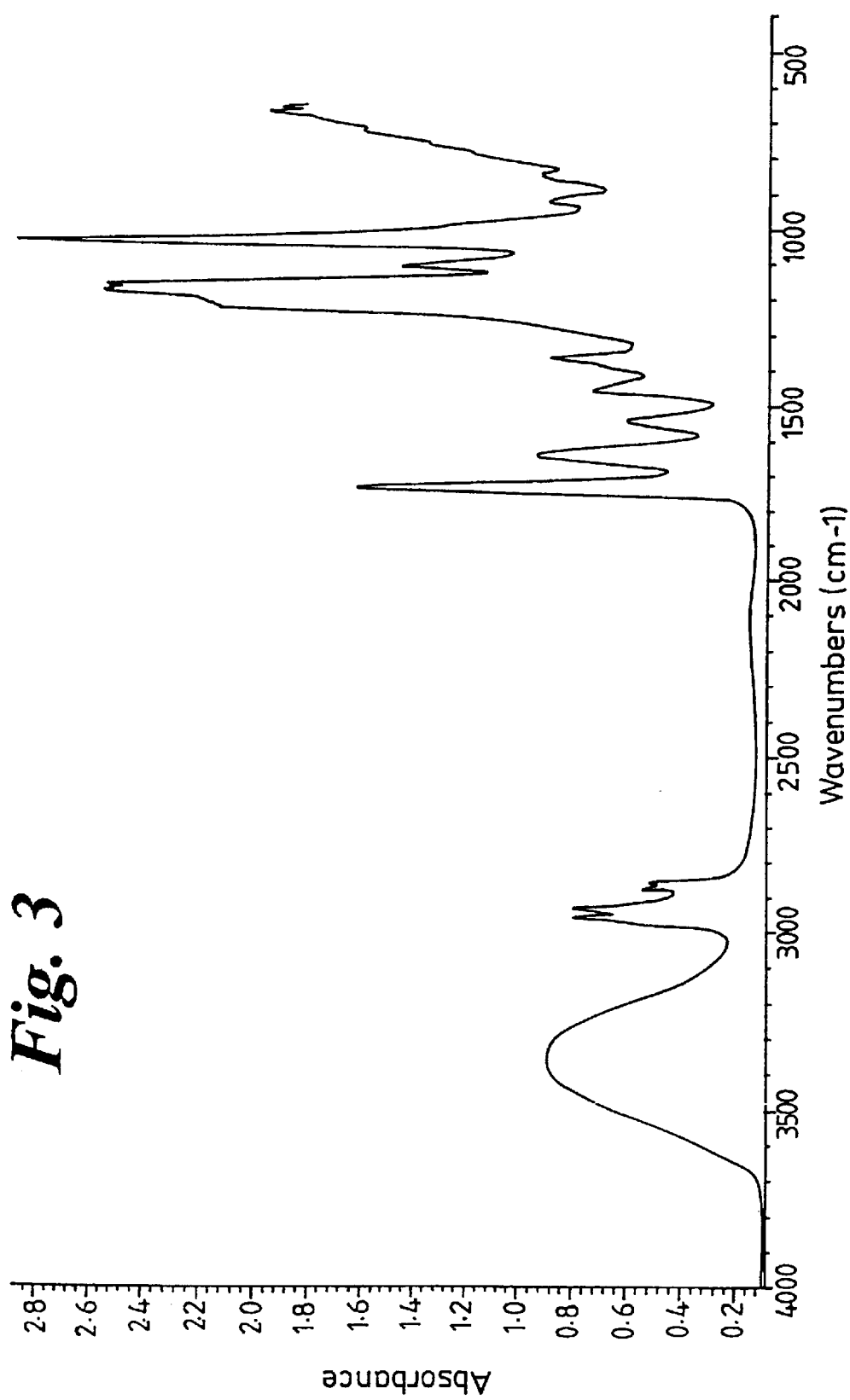
FIG. 3 is a graph showing Fourier transform infrared attenuated total reflectance spectra (FTIR ATR) of the gel formed after polymerisation using a ZnSe crystal according to one embodiment of the invention.

Fourier transform infrared attenuated total reflectance spectra (FTIR ATR) were taken of both the pregel mixture and of the gel formed after polymerisation using a ZnSe crystal (approximate sampling depth 1 μm). The results obtained are shown in FIGS. 2 and 3, respectively. The peak at around 1740 cm$^{-1}$ corresponds to the hydrophobic polymer whereas the peak at around 1550 cm$^{-1}$ corresponds to NaAMPS. It can be seen that before polymerisation the ratio in height of the former peak to the latter peak is about 0.25:1 whereas after polymerisation, the ratio is about 2.9:1. This shows a twelve-fold increase in the concentration of the hydrophobic polymer at the surface of the gel after polymerisation indicating that the hydrophobic polymer surface segregates. A further FTIR ATR spectrum was taken of the gel formed after polymerisation using a germanium crystal (approximate sampling depth 0.25μm). It was found that the ratio in the height of the former peak to the latter peak is 3.9:1 showing a sixteen fold increase in the concentration of the hydrophobic polymer on the surface of the gel.

To prepare formulation 13b, the same method used for formulation 13a was repeated except that a hydrophobic ethylene/vinyl acetate copolymer emulsion (50% solids) (product of Harlow Chemicals marketed under the trade name DM137) was used instead of Flexbond 150, 3 parts polyethylene glycol (molecular weight 600) were added with the hydrophobic copolymer DM137 and the parts by weight were changed to the figures given in Table 1.

Figure 4:
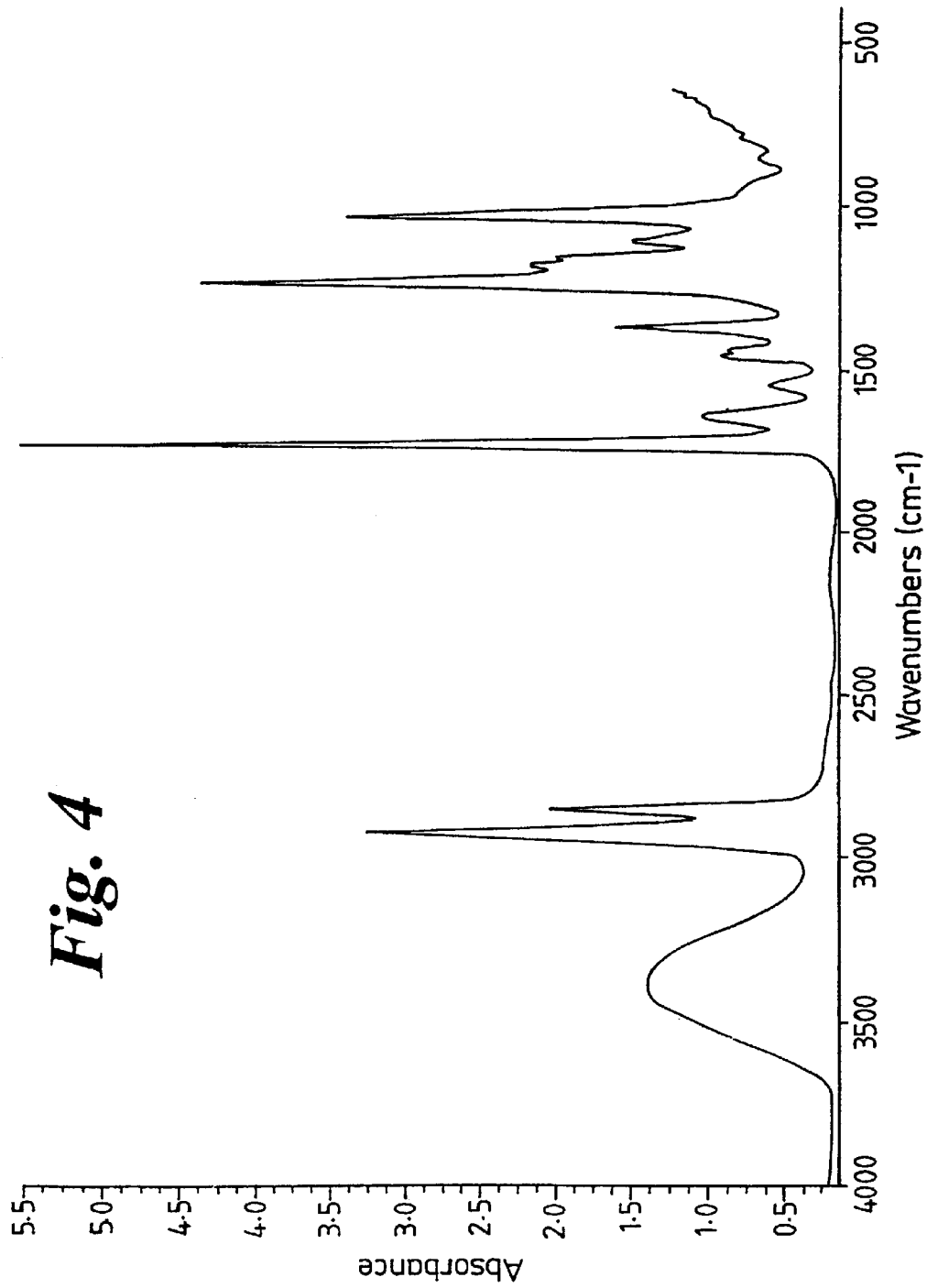
FIG. 4 is a graph showing FTIR ATR taken of the gel formed after polymerisation using a ZnSe crystal according to one embodiment of the invention.
Figure 5:
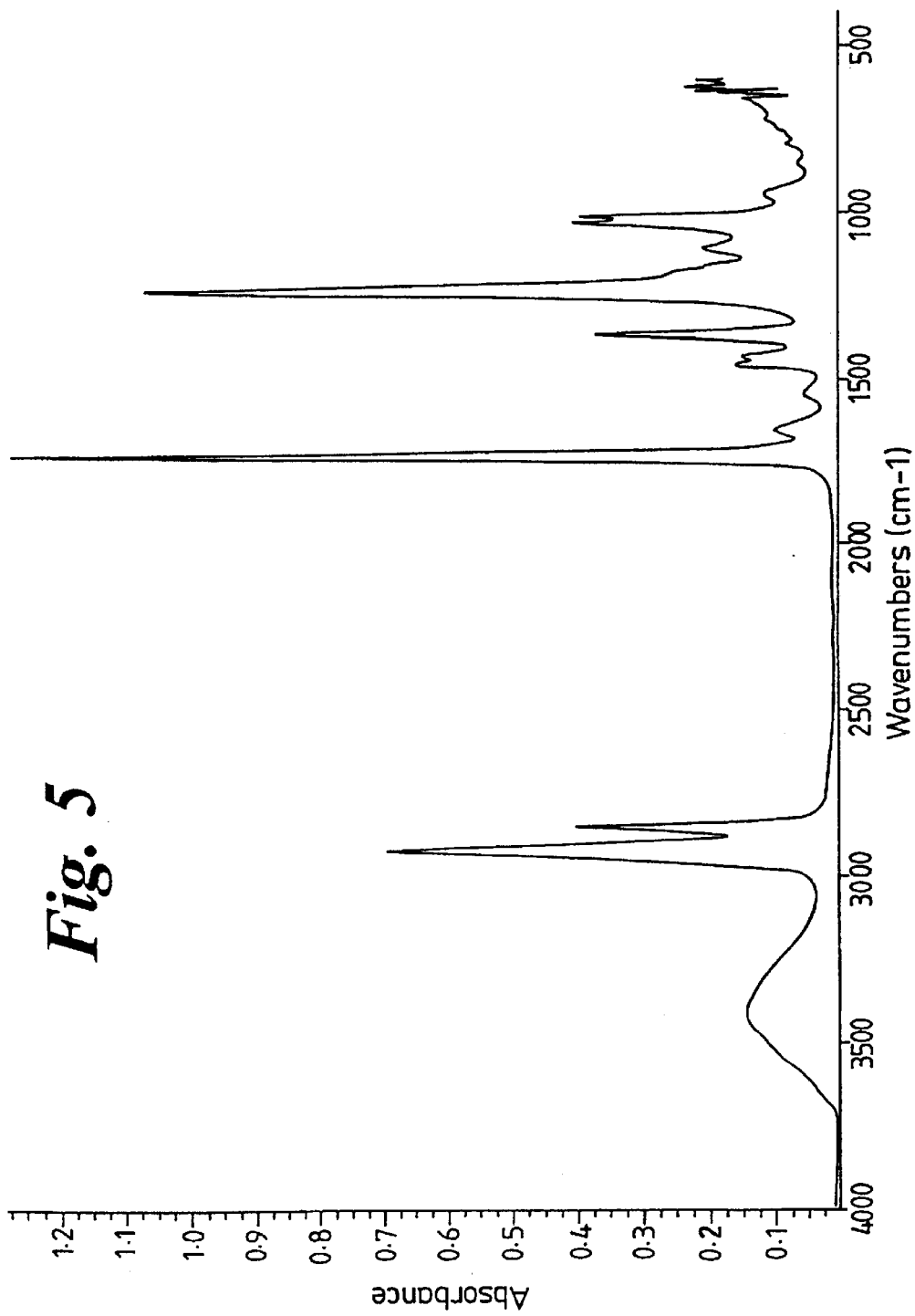
FIG. 5 is a graph showing a FTIR ATR taken of the gel formed after polymerisation using a germanium crystal according to one embodiment of the invention.

FTIR ATR were taken of the gel formed after polymerisation using a ZnSe crystal (approximate sampling depth 1 μm) and a germanium crystal (approximate sampling depth 0.25 μm). The results obtained are shown in FIGS. 4 and 5, respectively. As for formulation 10a, the peak at around 1740 cm$^{-1}$ corresponds to the hydrophobic polymer whereas the peak at around 1550 cm.$^{-1}$ corresponds to NaAMPS. The ratio of the former peak to the latter peak for FIG. 4 (the ZnSe FTIR ATR spectrum) is about 21:1 whereas the ratio for FIG. 5 (the germanium FTIR ATR spectrum) is about 11:1. This again demonstrates the hydrophobic polymer segregates to the surface of the gel.

To prepare formulation 13c, the same method used for formulation 13a was repeated except that a hydrophobic ethylene/vinyl acetate copolymer emulsion (50% solids) (product of Harlow Chemicals marketed under the trade name DM137) was used instead of Flexbond 150, 0.05 parts of sodium nitrate were added with the potassium chloride and the parts by weight were changed to the figures given in Table 1.

To prepare formulations 13d and 13e, the same method used for formulation 13b was repeated except that solution A as described in Example 1 was used instead of solution C and the parts by weight were changed to the figures given in Table 1.

To prepare formulations 13f and 13g, the same method used for formulation 13d was repeated except that potassium chloride was omitted and the parts by weight were changed to the figures given in Table 1.

TABLE 1

| COMPOSITION by WEIGHT | | | | | | | |
|---|---|---|---|---|---|---|---|
| Formulation | 13a | 13b | 13c | 13d | 13e | 13f | 13g |
| 58% NaAMPS | 44 | 44 | 65 | 35 | 35 | 35 | 37 |
| KCl | 4 | 5 | 5 | 5 | 5 | | |
| SPA | 20 | 20 | 10 | 25 | 25 | 15 | 18 |
| Glycerol | 20 | 20 | 23 | 20 | 20 | 30 | 30 |
| Gum Arabic | | | | | | | |
| DM 137 | | 15 | 2 | 15 | 15 | 15 | 10 |
| Flexbond 150 | 15 | | | | | | |
| PEG 600 | | 3 | | 10 | 10 | 5 | 5 |
| Sodium Nitrate | | | 0.05 | | | | |
| PI/XL | 0.13 | 0.13 | 0.15 | 0.12 | 0.13 | 0.15 | 0.15 |
| (Solution) | (C) | (C) | (C) | (A) | (A) | (A) | (A) |
| G'(@ 1 rad/s) | 6156 | 4756 | | | | | |
| G'(@ 100 rad/s) | 15219 | 15412 | | | | | |
| G"(@ 1 rad/s) | 1775 | 1840 | | | | | |
| G"(@ 100 rad/s) | 5748 | 7743 | | | | | |

To prepare formulations 13h. 13i and 13j the same method used for formulation 13g was repeated except that the parts by weight were changed to the figures given in Table 2.

To prepare formulations 13k, 13l and 13m, the same method used for formulation 13j was repeated except that a propylene oxide/ethylene oxide block copolymer surfactant (designated PE/F127 and manufactured by BASF) was added with the glycerol and the parts by weight were changed to the figures given in Table 2.

TABLE 2

| COMPOSITION by WEIGHT | | | | | | |
|---|---|---|---|---|---|---|
| Formulation | 13h | 13i | 13j | 13k | 13l | 13m |
| 58% NaAMPS | 37 | 35 | 35 | 35 | 35 | 35 |
| SPA | 18 | 15 | 25 | 25 | 25 | 25 |
| Glycerol | 30 | 33 | 20 | 20 | 20 | 20 |
| DM 137 | 10 | 10 | 15 | 15 | 15 | 15 |
| PEG 600 | 10 | 5 | 10 | 10 | 10 | 10 |
| PE/F127 | | | | 1 | 5 | 9 |
| PI/XL (Solution) | 0.15 (A) | 0.15 (A) | 0.14 (A) | 0.14 (A) | 0.14 (A) | 0.14 (A) |

EXAMPLE 14

To 33 parts glycerol, 10 parts of an ethylene/vinyl acetate copolymer emulsion (50% solids) (product of Harlow Chemicals marketed under the trade name DM137) were added and stirred until a uniform colour was obtained. To this mixture were added 50 parts of a 75% aqueous solution of (3-acrylamidopropyl)trimethyl ammonium chloride sold by Aldrich and 5 parts of polyethylene glycol (molecular weight 600), and the solution was heated with stirring to 60°C. for one hour. The solution was cooled to 20° C. and then there was added 0.15 parts of solution A prepared as described in Example 1. This final solution was stirred for one hour and then cured as in Example 1. The G' and G" moduli were measured from 20 mm diameter discs of the gel using a Rheometric Scientific RS-5 rheometer at 37° C.

EXAMPLE 15

An aqueous reaction mixture (or so-called pregel) was prepared as described in Example 1 and coated onto a siliconised release paper at a coat weight of 0.8 kilograms per square meter. The aqueous reaction mixture was cured by passing the assembly under a medium pressure mercury arc lamp at a speed of 5 meters per minute. The residence time under the lamp was 4 seconds. The cured bioadhesive composition was then laminated by a polyurethane film (sold under the trade name SRF076 part number 93034 by Advanced Medical Solutions) to form a wound dressing.

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

What is claimed is:

1. A bioadhesive composition which comprises an aqueous plasticised three dimensional polymeric matrix and a hydrophobic polymer, said aqueous plasticised three-dimensional polymeric matrix comprising up to 50% by weight of a plasticiser other than water and said matrix being the product of a polymerisation reaction performed in the presence of water, said plasticiser and said hydrophobic polymer, wherein concentration of said hydrophobic-polymer at surface of said matrix is greater than concentration of said hydrophobic polymer inside said matrix.

2. A bioadhesive composition according to claim 1 wherein said concentration of said hydrophobic polymer at surface of said matrix is four times greater than said concentration of said hydrophobic polymer inside said matrix.

3. A bioadhesive composition according to claim 2 wherein said concentration of said hydrophobic polymer at surface of said matrix is eight times greater than said concentration of said hydrophobic polymer inside said matrix.

4. A bioadhesive composition according to claim 1, comprising:
  (i) a water activity in the range of 0.4 to 0.9;
  (ii) an elastic modulus at 1 rad/s in the range of 700 to 15,000 Pa;
  (iii) an elastic modulus at 100 rad/s in the range of 2000 to 40,000 Pa;
  (iv) a viscous modulus at 1 rad/s in the range of 400 to 14,000 Pa; and
  (v) a viscous modulus at 100 rad/s in the range of 1000 to 35,000 Pa.

5. A bioadhesive composition according to claim 1, obtained by polymerising a re ion mixture comprising:
  (a) one or more monomers comprising a hydrophilic unsaturated water soluble acrylamido monomer;
  (b) a hydrophobic polymer; and
  (c) a plasticiser.

6. A bioadhesive composition according to claim 5 obtained by polymerising a reaction mixture comprising (a) 20% to 55% by weight of said one or more monomers comprising a hydrophilic unsaturated water-soluble acrylamide monomer, (b) 0.1% to 10% by weight of said hydrophobic polymer and (c) 35% to 70% by weight of said plasticiser.

7. A bioadhesive composition according to claim 5 or claim 6 wherein said one or more monomers further comprise an ionic hydrophilic unsaturated water-soluble monomer or a non-ionic hydrophilic unsaturated water-soluble monomer.

8. A bioadhesive composition according to claim 1 wherein said hydrophobic polymer is a hydrophobic pressure sensitive adhesive.

9. A bioadhesive composition according to claim 5 wherein the reaction mixture additionally comprises from 1 to 10% by weight of a crosslinker.

10. A bioadhesive composition according to claim 9 wherein said crosslinker is selected from the group consisting of tripropylene glycol diacrylate, ethylene glycol dimethacrylate, triacrylate, polyethylene glycol diacrylate, methylene bis acrylamide, and combinations thereof.

11. A bioadhesive composition according to claim 5 wherein said reaction mixture additionally comprises an interpenetrant polymer in an amount from 1 to 6% by weight.

12. A bioadhesive composition according to claim 11 wherein the interpenetrant polymer is selected from the group consisting of poly 2-acrylamido-2-methyl-propane sulphonic acid (AMPS), poly 3-sulpho-propyl acrylate (SPA), a copolymer of sodium salt of 2-acrylamido-2-methyl-propane sulphonic acid (NaAMPS) and SPA, polyacrylic acid, polymethacrylic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl ethacrylate and vinylcaprolactam, natural polysaccharides, synthetic polysaccharides, carboxymethyl cellulose, sodium carboxymethyl cellulose, hydroxypropylmethy cellulose, hydroxyethyl cellulose and combinations thereof.

13. A bioadhesive composition according to claim 5 wherein said reaction mixture additionally corn rises from 1 to 7% by weight of a salt.

14. A pair of biomedical electrodes which comprise a bioadhesive composition according to claim 1.

15. A pair of biomedical electrodes which comprise bioadhesive composition according to any one of the preceding claims.

16. A fixation product for attaching a biomedical device to skin which comprises a bioadhesive composition according to claim 1.

17. A wound dressing which comprises a carrier material in association with a bioadhesive composition of claim 1.

18. A bioadhesive composition according to claim 1, wherein said three dimensional polymeric matrix comprises a polymer or copolymer of a hydrophilic water-soluble acrylamido monomer of formula

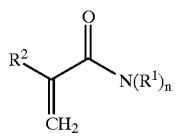

(I)

wherein: n represents 2 or 3, provided that when n represents 3 a counterion is also present; $R^1$ represents H, $C_{1-4}$-alkyl or $R^8SO_3M$ wherein $R^8$ represents an optionally substituted hydrocarbon moiety and M represents hydrogen or a cation, each $R^1$ being mutually the same or different; and $R^2$ is hydrogen or optionally substituted methyl or ethyl.

19. A bioadhesive composition according to claim 18, wherein in said hydrophilic water-soluble acrylamido monomer of formula I, said hydrocarbon moiety or said methyl or ethyl group, when substituted, is substituted by a substituent selected from the group consisting of hydroxyl, amino, ammonium and halogen.

20. A bioadhesive composition according to claim 18, wherein in said hydrophilic water-soluble acrylamido monomer of formula I, said cation, when present, is an alkali metal cation.

21. A bioadhesive composition according to claim 18, wherein in said hydrophilic water-soluble acrylamido monomer of formula I: n represents 2; $R^1$ represents H or $R^8SO_3M$ wherein $R^8$ represents an optionally substituted hydrocarbon moiety and M represents hydrogen or a cation, each $R^1$ being mutually the same or different; and $R^2$ is hydrogen or optionally substituted methyl or ethyl.

22. A bioadhesive composition according to claim 18, wherein in said hydrophilic water-soluble acrylamido monomer of formula I at least one $R^1$ represents $R^8SO_3M$ wherein $R^3$ represents an optionally substituted alkyl, cycloalkyl or aromatic moiety and M represents hydrogen or a cation.

23. A bioadhesive composition according to claim 22, wherein $R^8$ contains from 3 to 12 carbon atoms.

24. A bioadhesive composition according to claim 22, wherein $R^8$ contains from 3 to 6 carbon atoms.

25. A bioadhesive composition according to claim 22, wherein $R^8$ represents a moiety of the formula

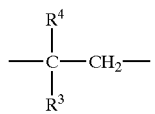

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

26. A bioadhesive composition according to claim 25, wherein in said $R^8$ moiety said straight or branched chain alkyl group, when present, is substituted by a substituent selected from the group consisting of hydroxyl, amino, ammonium and halogen.

27. A bioadhesive composition according to claim 18, wherein in said hydrophilic water-soluble acrylamido monomer of formula I: n represents 3; $R^1$ represents H or $C_{1-4}$-alkyl, each $R^1$ being mutually the same or different; and $R^2$ is hydrogen or optionally substituted methyl or ethyl.

28. A bioadhesive composition according to claim 18, wherein said hydrophilic water-soluble acrylamido monomer comprises 2-acrylamido-2-methylpropane sulphonic acid or a salt thereof.

29. A bioadhesive composition according to claim 28, wherein said salt is selected from the group consisting of sodium, potassium and lithium salts.

30. A bioadhesive composition according to claim 18, wherein said hydrophilic water-soluble acrylamido monomer comprises (3-acrylamidopropyl) trimethyl ammonium chloride.

31. A bioadhesive composition according to claim 18, wherein said three dimensional polymeric matrix further comprises a polymer or copolymer of an ionic or non-ionic hydrophilic unsaturated water-soluble monomer compound of formula

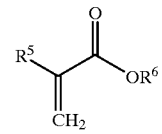

(II)

wherein: $R^5$ represents hydrogen or optionally substituted methyl or ethyl; and $R^6$ represents hydrogen, a cation or $R^7SO_3$ wherein $R^7$ represents an optionally substituted alkylene moiety of 1 to 4 carbon atoms.

32. A bioadhesive composition according to claim 31, wherein said methyl or ethyl group or said alkylene moiety, when present, is substituted by a substituent selected from the group consisting of hydroxyl, amino, ammonium and halogen.

33. A bioadhesive composition according to claim 31, wherein $R^7$ represents an optionally substituted n-propyl group.

34. A bioadhesive composition according to claim 31, wherein said ionic hydrophilic unsaturated water-soluble monomer is selected from the group consisting of acrylic acid or an ester or salt thereof, a polymerisable sulphonate or salt thereof, and mixtures thereof.

35. A bioadhesive composition according to claim 34, wherein said ionic hydrophilic unsaturated water-soluble monomer comprises acrylic acid (3-sulphopropyl) ester or a salt thereof.

36. A bioadhesive composition according to claim 35, wherein said salt is selected from the group consisting of sodium, potassium and lithium salts.

37. A bioadhesive composition according to claim 1, wherein said hydrophobic polymer is selected from the group consisting of a polyacrylate, a polyolefin, a silicone adhesive, a natural rubber, a synthetic rubber, a polyvinyl ether, and mixtures thereof.

38. A bioadhesive composition according to claim 1, wherein said hydrophobic polymer comprises a vinyl acetate dioctyl maleate copolymer.

39. A bioadhesive composition according to claim 1, wherein said hydrophobic polymer comprises an ethylene vinyl acetate copolymer.

40. A bioadhesive composition according to claim 1, wherein said aqueous plasticised three dimensional polymeric matrix includes an aqueous plasticising medium.

41. A bioadhesive composition according to wherein said aqueous plasticising medium comprises water and a plasticiser, said plasticiser is selected from the group consisting of a polyhydric alcohol, an ester derived therefrom, a polymeric alcohol, and mixtures thereof.

42. A bioadhesive composition according to claim 5, wherein said plasticiser comprises water and a plasticiser selected from the group consisting of a polyhydric alcohol, an ester derived therefrom, a polymeric alcohol, and mixtures thereof.

43. A bioadhesive composition according to claim 1, further comprising an additional component selected from the group consisting of crosslinkers, interpenetrant polymers, surfactants, electrolytes, processing aids, antimicrobial agents, pharmaceutically active agents and mixtures thereof.

44. A bioadhesive composition according to claim 1, obtained by polymerising a reaction mixture comprising (a) a monomer mixture comprising a hydrophilic unsaturated water-soluble acrylamido monomer and an ionic monomer selected from the group consisting of acrylic acid, an ester or salt thereof, a polymerisable sulphonate or salt thereof, and mixtures thereof, (b) a hydrophobic polymer, and (c) a plasticiser.

45. A bioadhesive composition according to claim 5 or 44, wherein plasticiser comprises water and a plasticiser selected from the group consisting of a polyhydric alcohol, an ester derived therefrom, a polymeric alcohol and mixtures thereof.

46. A bioadhesive compostion according to claim 5, wherein said reaction mixture further includes components selected from the group consisting of crosslinkers, interpenetrant polymers, surfactants, electrolytes, processing aids, antimicrobial agents, pharmaceutically active agents and mixtures thereof.

47. A bioadhesive composition according to claim 44, wherein said hydrophobic polymer Comprises a vinyl acetate dioctyl maleate copolymer.

48. A bioadhesive composition according to claim 44, wherein said hydrophobic polymer comprises an ethylene vinyl acetate copolymer.

49. A biomedical electrode comprising an electrically conductive interface member adapted to be connected electrically to an item of medical equipment and an electrically conductive medium associated with the interface member for adhering to a patient's skin, wherein said electrically conductive medium comprises a bioadhesive composition comprising an aqueous plasticised three dimensional polymeric matrix and a hydrophobic polymer said aqueous plasticised three-dimensional polymeric matrix comprising up to 50% by weight of a plasticiser other than water and said matrix being the product of a polymerisation reaction performed in the presence of said water, said plasticiser and said hydrophobic polymer, wherein concentration of said hydrophobic polymer at surface of said matrix is greater than concentration of said hydrophobic polymer inside said matrix.

50. A biomedical electrode according to claim 49, wherein said electrically conductive interface comprises a layer of an electrically conductive material applied to a support member.

51. A biomedical electrode according to claim 49, wherein said bioadhesive composition is obtained by polymerising a reaction mixture comprising (a) one or more monomers comprising a hydrophilic unsaturated water soluble acrylamido monomer; (b) a hydrophobic polymer; and (c) a plasticiser.

52. A biomedical electrode according to 49, said bioadhesive composition is obtained by polymerising a reaction mixture comprising (a) a monomer mixture comprising a hydrophilic unsaturated water-soluble acrylamido monomer and an ionic monomer selected from the group consisting of acrylic acid, an ester or salt thereof, a polymerisable sulphonate or salt thereof, and mixtures thereof, (b) a hydrophobic polymer, and (c) a plasticiser.

53. A biomedical electrode according to claim 51 or 52, where said plasticiser is mixed with water and said plasticiser is selected from the group consisting of a polyhydric alcohol, an ester derived therefrom, a polymeric alcohol and mixtures thereof.

54. A biomedical electrode according to claim 51 or 52, wherein said reaction mixture further includes components selected from the group consisting of crosslinkers, intrepenetrant polymers, surfactants, electrolytes, processing aids, antimicrobial agents, pharmaceutically active agents and mixtures thereof.

55. A fixation product for attaching a catheter, tubing, wires or cables to skin, wherein a bioadhesive composition is provided at a point of said attachment, said bioadhesive composition comprising an aqueous plasticised three dimensional polymeric matrix and a hydrophobic, said aqueous plasticised three-dimensional polymeric matrix comprising up to 50% by weight of a plasticiser other than water and said matrix being the product of a polymerisation reaction performed in the presence of water, said plasticiser and said hydrophobic polymer, wherein concentration of said hydrophobic polymer at surface of said matrix is greater than concentration of said hydrophobic polymer inside said matrix.

56. A fixation product according to claim 55, wherein said bioadhesive composition is obtained by polymerising a reaction mixture comprising: (a) one or more monomers comprising a hydrophilic unsaturated water soluble acrylamido monomer; (b) a hydrophobic polymer; and (c) a plasticiser.

57. A fixation product according to claim 55, wherein said bioadhesive composition is obtained by polymerising a reaction mixture comprising (a) a monomer mixture comprising a hydrophilic unsaturated water-soluble acrylamido monomer and an ionic monomer selected from the group consisting of acrylic acid, an ester or salt thereof, a polymerisable sulphonate or salt thereof, and mixtures thereof, (b) a hydrophobic polymer, and (c) a plasticiser.

58. A fixation product according to claim 56 or 57, wherein said plasticiser is mixed with waters and said plasticiser is selected from the group consisting of a polyhydric alcohol, an ester derived therefrom, a polymeric alcohol and mixtures thereof.

59. A fixation product according to claim 56 or 57, wherein said reaction mixture further includes components selected from the group consisting of crosslinkers, interpenetrant polymers, surfactants, electrolytes, processing aids, antimicrobial agents, pharmaceutically active agents and mixtures thereof.

60. A wound dressing comprising a carrier material encapsulated or coated by a bioadhesive composition comprising an aqueous plasticised three dimensional polymeric matrix and a hydrophobic polymer, said aqueous plasticised three-dimensional polymeric matrix comprising up to 50% by weight of a plasticiser other than water and said matrix being the product of a polymerisation reaction performed in the presence of water, said plasticiser and said hydrophobic polymer, wherein concentration of said hydrophobic polymer at surface of said matrix is greater than concentration of said hydrophobic polymer inside said matrix.

61. A wound dressing according to claim 60, wherein said bioadhesive composition is obtained by polymerising an aqueous reaction mixture comprising: (a) one or more monomers comprising a hydrophilic unsaturated water soluble acrylamido monomer; (b) a hydrophobic polymer; and (c) a plasticiser.

62. A wound dressing according to claim 60, wherein said bioadhesive composition is obtained by polymerising an aqueous reaction mixture comprising (a) a monomer mixture comprising a hydrophilic unsaturated water-soluble acrylamido monomer and an ionic monomer selected from the group consisting of acrylic acid, an ester or salt thereof, a polymerisable sulphonate or salt thereof, and mixtures thereof, (b) a hydrophobic polymer, and (c) a plasticiser.

63. A wound dressing according to claim 61 or 62, wherein said plasticiser is mixed with water and said plasticiser is selected from the group consisting of a polyhydric alcohol, an ester derived therefrom, a polymeric alcohol and mixtures thereof.

64. A wound dressing according to claim 61 or 62, wherein said aqueous reaction mixture further includes components selected from the group consisting of crosslinkers, interpenetrant polymers, surfactants, electrolytes, processing aids, antimicrobial agents, pharmaceutically active agents and mixtures thereof.

65. A wound dressing according to claim 61 or 62, when prepared by coating or encapsulating said carrier material with said aqueous reaction mixture, said aqueous reaction mixture comprising first and second monomers and a crosslinking agent, and curing said coating on said carrier material.

66. A wound dressing according to claim 60, when prepared by coating said carrier material with said bioadhesive composition.

67. A bioadhesive composition obtained by polymerising an aqueous reaction mixture comprising (a) a monomer mixture comprising a hydrophilic unsaturated water-soluble acrylamido monomer and an ionic monomer selected from the group consisting of acrylic acid; an ester or salt thereof, a polymerisable sulphonate or salt thereof, and mixtures thereof, (b) a hydrophobic polymer, and (c) a plasticiser.

68. A bioadhesive composition according to claim 67, wherein said plasticiser comprises water and a plasticiser selected ft of a polyhydric alcohol, an ester derived therefrom, a polymeric alcohol and mixtures thereof.

69. A bioadhesive composition according to claim 68, wherein said aqueous reaction mixture further includes components selected from the group consisting of crosslinkers, interpenetrant polymers, surfactants, electrolytes, processing aids, antimicrobial agents, pharmaceutically active agents and mixtures thereof.

* * * * *

UNITED STATES PATENT AND TRADEMARK OFFICE
CERTIFICATE OF CORRECTION

PATENT NO. : 6,592,898 B2
DATED : July 15, 2003
INVENTOR(S) : Munro et al.

It is certified that error appears in the above-identified patent and that said Letters Patent is hereby corrected as shown below:

Column 20,
Lines 58-62, claim 41 should read:
41. A bioadhesive composition according to claim 40, wherein said aqueous plasticising medium comprises water and a plasticiser, said plasticiser is selected from the group consisting of a polyhydric alcohol, an ester derived therefrom, a polymeric alcohol, and mixtures thereof.

Column 21,
Lines 58-65, claim 52 should read:
52. A biomedical electrode according to claim 49, wherein said bioadhesive composition is obtained by polymerising a reaction mixture comprising (a) a monomer mixture comprising a hydrophilic unsaturated water-soluble acrylamido monomer and an ionic monomer selected from the group consisting of acrylic acid, an ester or salt thereof, a polymerisable sulphonate or salt thereof, and mixtures thereof, (b) a hydrophobic polymer, and (c) a plasticiser.

Column 24,
Lines 15-20, claim 69 should read:
69. A bioadhesive composition according to claim 67, wherein said aqueous reaction mixture further includes components selected from the group consisting of crosslinkers, interpenetrant polymers, surfactants, electrolytes, processing aids, antimicrobial agents, pharmaceutically active agents and mixtures thereof.

Signed and Sealed this

Twenty-fifth Day of November, 2003

JAMES E. ROGAN
*Director of the United States Patent and Trademark Office*